United States Patent [19]

Nedelec et al.

[11] 4,148,919

[45] Apr. 10, 1979

[54] 7-AMINO-6,7-DIHYDRO [5H]BENZOCYCLOHEPTENE DERIVATIVES

[75] Inventors: Lucien Nedelec, Le Raincy; André Pierdet, Noisy-le-Sec; Claude Dumont, Nogent-sur-Marne; Marie-Hélène Kannengiesser, Paris, all of France

[73] Assignee: Roussel Uclaf, Paris, France

[21] Appl. No.: 708,750

[22] Filed: Jul. 26, 1976

[30] Foreign Application Priority Data

Jul. 28, 1975 [FR] France .................................. 75 23500

[51] Int. Cl.² .......................... A01N 9/20; A01N 9/24; C07C 87/28
[52] U.S. Cl. ............................. 424/33 D; 260/501.1; 260/501.11; 260/501.18; 260/501.19; 260/501.21; 260/570.8 R; 260/570.9; 260/571; 260/578; 260/590 FA; 424/316
[58] Field of Search ..................... 260/578, 570.9, 571, 260/575; 424/330, 316

[56] References Cited

U.S. PATENT DOCUMENTS

| | | | |
|---|---|---|---|
| 2,794,048 | 5/1957 | Richter et al. | 260/570.9 |
| 3,201,470 | 8/1965 | Huebner | 260/577 |
| 3,458,577 | 7/1969 | Galantay | 260/571 |
| 3,922,305 | 11/1975 | Engelhardt | 260/570.8 |

OTHER PUBLICATIONS

Levshine et al., "Chemical Abstracts", vol. 55, p. 21066d (1961).
Carlsson et al., "Chemical Abstracts", vol. 63, p. 2276 (1965).

*Primary Examiner*—Robert V. Hines
*Attorney, Agent, or Firm*—Hammond & Littell

[57] ABSTRACT

7-amino-6,7-dihydro [5H] benzocycloheptenes of the formula

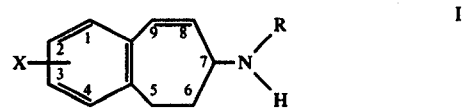

wherein X is selected from the group consisting of hydrogen, chlorine, bromine and iodine in 2- or 4- position of the ring when halogen and R is selected from the group consisting of hydrogen and phenyl alkyl of 7 to 10 carbon atoms and their non-toxic, pharmaceutically acceptable acid addition salts having antidepressive activity and a process for their preparation and novel intermediates.

5 Claims, No Drawings

7-AMINO-6,7-DIHYDRO [5H]BENZOCYCLOHEPTENE DERIVATIVES

OBJECTS OF THE INVENTION

It is an object of the invention to provide the 7-amino-6,7-dihydro benzocycloheptenes of formula I and their non-toxic, pharmaceutically acceptable acid addition salts.

It is another object of the invention to provide a novel process for the preparation of the compounds of formula I and novel intermediates therefore.

It is a further object of the invention to provide novel antidepressive compositions and to a novel method of relieving depression in warm-blooded animals.

These and other objects and advantages of the invention will become obvious from the following detailed description.

THE INVENTION

The novel compounds of the invention are selected from the group consisting of 7amino-6,7dihydro [5H] benzocycloheptenes of the formula

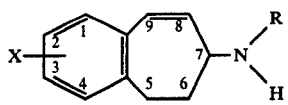

wherein X is selected from the group consisting of hydrogen, chlorine, bromine and iodine in 2- or 4- position of the ring when halogen and R is selected from the group consisting of hydrogen and phenyl alkyl of 7 to 10 carbon atoms and their non-toxic, pharmaceutically acceptable acid addition salts.

In the compounds of formula I, X is preferably bromine or chlorine and examples of phenyl alkyl for R are benzyl, phenethyl, 3-phenylpropyl and 2-phenylpropyl. Preferably, R is hydrogen, benzyl or phenethyl. A preferred compound is 7-amino-6,7-dihydro [5H] benzocylcoheptene and its non-toxic, pharmaceutically acceptable acid addition salts.

Examples of suitable acids for the preparation of the non-toxic, pharmaceutically acceptable acid addition salts are mineral acids like hydrochloric acid, hydrobromic acid, hydroiodic acid, nitric acid, sulfuric acid and phosphoric acid and organic acids such as acetic acid, formic acid, benzoic acid, maleic acid, fumaric acid, succinic acid, tartaric acid, citric acid, oxalic acid, glyoxylic acid, aspartic acid, alkanesulfonic acids like methanesulfonic acid and arylsulfonic acids like benzenesulfonic acid.

The process of the invention for the preparation of the compounds of formula I comprises reacting a compound of the formula

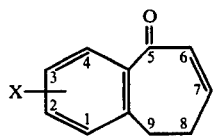

wherein X has the above definition with a phenylalkylamine of the formula

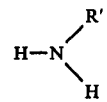

wherein R' is phenylalkyl of 7 to 10 carbon atoms to form a compound of the formula

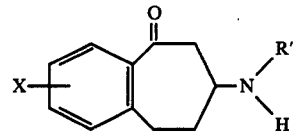

reducing the said compound to obtain a compound of the formula

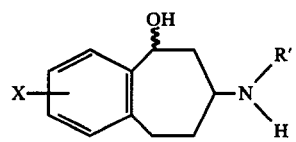

and dehydrating the latter compound to form the corresponding compound of formula I wherein R is phenylalkyl of 7 to 10 carbon atoms which, if desired, may be salified. When R' is benzyl, the compound of formula V may be subjected to hydrogenolysis to form a compound of the formula

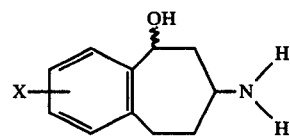

which is then dehydrated to obtain the corresponding compounds of formula I wherein R is hydrogen and if desired, it may be salified.

In a preferred mode of the process of the invention, the reaction between the compounds of formulae II and III is effected at room temperature in a lower alkanol such as ethanol and the reduction of the compound of formula IV is effected with a metal hydride such as lithium aluminum hydride in an organic solvent such as tetrahydrofuran. The dehydration of the compounds of formulae V and VI is effected in an organic solvent such as dioxane at reflux with a strong acid such as hydrochloric acid or sulfuric acid or with potassium bisulfate or by heating in hexametapol. The hydrogenolysis of the compound of formula V is effected with hydrogen in the presence of a catalyst such as palladium.

The acid addition salts of the compounds of formula I may be prepared by reacting substantially stoichiometric amounts of the acid and the free base with or without separation of the free base.

The starting materials of formula II wherein X is other than hydrogen, when they are not known may be prepared by reacting a compound of the formula

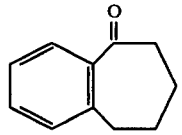

with a halogenation agent other than a fluorination agent to obtain a compound of the formula

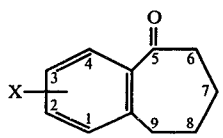

wherein X is chlorine, bromine or iodine in the 1- or 3-position, reacting the latter with cupric bromide, bromine or a complex of bromine such as pyridinium perbromide in an organic solvent to form a compound of the formula

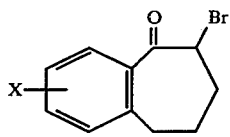

which is dehydrobrominated in the presence of lithium bromide and lithium carbonate to obtain the corresponding compound of formula II.

The novel intermediates produced in the process of the invention are those of formula IV and particularly 7-benzylamino-6,7,8,9-tetrahydro [5H] benzocyclohepten-5-one and compounds of the formula

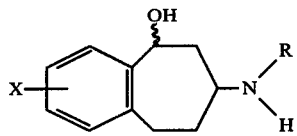

wherein X and R have the above definition and particularly the A and B isomers of 5-hydroxy-7-benzylamino-6,7,8,9-tetrahydro [5H] benzocycloheptene and the A and B isomers of 5-hydroxy-7-amino-6,7,8,9-tetrahydro [5H] benzocycloheptene.

The novel antidepressive compositions of the invention are comprised of an effective amount of at least one compound of formula I or its non-toxic, pharmaceutically acceptable acid addition and a non-toxic, pharmaceutical carrier. The compositions may be in the form of tablets, dragees, gelules, granules, suppositories and injectable solutions of suspensions formed in the usual manner.

Examples of suitable carriers or excipients are talc, arabic gum, lactose, starch, magnesium stearate, cacao butter, aqueous or non-aqueous vehicles, fatty bodies of animal or vegetable origin, paraffinic derivatives, glycols, preservatives and diverse wetting agents, dispersants and emulsifiers.

The compositions of the invention are useful for the treatment of depression, melancoly, manic-depressive psychoses, reactionnal depressions, depressions due to exhaustion, neurotic depressions and for the treatment of the symptoms of Parkinson disease. Particularly preferred is 7-amino-6,7-dihydro /5H/ benzocycloheptene and its non-toxic, pharmaceutically acceptable acid addition salts at an oral dose of 10 to 300 mg per day in humans. The novel method of the invention for the treatment of depressed states and psychoses in warm-blooded animals including humans comprises administering to warm-blooded animals an antidepressively effective amount of at least one compound of formula I and its non-toxic, pharmaceutically acceptable acid addition salts. The compounds may be administered orally, rectally or parenterally and the usual useful dose is 0.2 to 6 mg/kg depending upon the product and the method of administration.

In the following examples there are described several preferred embodiments to illustrate the invention. However, it is to be understood that the invention is not intended to be limited to the specific embodiments.

EXAMPLE 1

7-amino-6,7-dihydro [5H] benzocycloheptene-hydrochloride

STEP A: 7-benzylamino-6,7,8,9-tetrahydro [5H] benzocyclohepten-5-one and its hydrochloride A mixture of 10 g of 8,9-dihydro [5H] benzocyclohepten-5-one in 100 ml of absolute ethanol and 10 ml of benzylamine was stirred at 20°–25° C. for 2 hours and the solvent and excess benzylamine were evaporated under reduced pressure at 40° C. to obtain 20 g of raw product. The latter was chromatographed over silica gel and was eluted with a 7-3-1 cyclohexane-ethyl acetate-triethylamine mixture to obtain 13.4 g of product. The latter was chromatographed over silica gel under a pressure of 2 kg to obtain 9 g of 7-benzylamino-6,7,8,9-tetrahydro [5H] benzocyclohepten-5-one in the form of an oil.

For analysis, a solution of ether saturated with hydrochloric acid was added to a solution of 200 mg of the latter product in ether and the mixture was filtered. The recovered precipitate was washed with ether and dried under reduced pressure to obtain 200 mg of 7-benzylamino-6,7,8,9-tetrahydro [5H] benzocyclohepten-5-one hydrochloride in the form of crystals melting at 195° C.

STEP B: 5ξ-hydroxy-7-benzylamino-6,7,8,9-tetrahydro [5H] benzocycloheptene

A mixture of 1.5 g of lithium aluminum hydride in 150 ml of anhydrous tetrahydrofuran was cooled to 0° C. and a solution of 8 g of 7-benzylamino-6,7,8,9-tetrahydro [5H] benzocyclohepten-5-one in 150 ml of tetrahydrofuran was added thereto over 30 minutes at 0° to 5° C. The mixture was stirred for 2 hours at 0° C. and was then poured into an aqueous solution saturated with ammonium chloride. The mixture was filtered and the filtrate was extracted with ethyl acetate. The extract was washed with an aqueous sodium chloride solution, was dried and filtered. The filtrate was evaporated to dryness under reduced pressure at 40° C. to 8.4 g of raw product which was a mixture of the A and B isomers of 5ξ-hydroxy-7-benzylamino-6,7,8,9-tetrahydro [5H] benzocycloheptene which was used as is for the next step.

STEP C: 5ξ-hydroxy-7-amino-6,7,8,9-tetrahydro [5H] benzocycloheptene 8 g of 10% palladized carbon were added to a mixture of 8.2 g of the product of Step B in 250 ml of absolute ethanol and the mixture was heated to 80° C. under a hydrogen atmosphere for 30 minutes. The mixture was filtered and the filter was washed with ethanol. The filtrate was evaporated to dryness under reduced pressure to obtain 5.6 g of a mixture of the two isomers of 5ξ-hydroxy-7-amino-6,7,8,9-tetrahydro [5H] benzocycloheptene in the form of resin which was used as is for the next step.

STEP D: 7-amino-6,7,-dihydro [5H] benzocycloheptene hydrochloride 12 ml of 18N sulfuric acid were added to a refluxing mixture of 5.6 g of the product of Step C and 60 ml of dioxane and the mixture was refluxed for 2 hours and then was cooled to 20° C. The mixture was poured into 300 ml of water and the neutral fraction was extracted with ether. The aqueous phase was made alkaline with sodium hydroxide addition and was extracted with ethyl acetate. The ethyl acetate extracts were washed with aqueous sodium chloride solution, dried, filtered and evaporated to dryness to obtain 5 g of raw product. The latter was chromatographed over silica gel and was eluted with an 8-2-1 ethyl acetate-benzene-triethylamine mixture to obtain 3 g of 7-amino-6,7-dihydro [5H] benzocycloheptene in the form of a brown oil.

The said product was dissolved in 200 ml of ether and an ether solution saturated with hydrochloric acid was added thereto. The mixture was filtered and the recovered precipitate was washed with ether and dried to obtain 2.7 g of 7-amino- 6,7-dihydro [5H] benzocycloheptene hydrochloride in the form of white crystals melting at 248° C.

Analysis: $C_{11}H_{14}NCl$;
Calculated: %C 67.51; %H 7.21; %N 7.16; %Cl 18.12.
Found: 67.4; 7.2; 6.9; 18.2.

EXAMPLE 2

1- and 3-chloro-5-oxo-8,9-dihydro [5H] benzocycloheptene

STEP A: 1- and 3-chloro-benzosuberone mixture 797 g of aluminum chloride were added over 20 minutes at 0° C. to a solution of 400 g of benzosuberone in 1600 ml of 1,1,2,2,-tetrachloroethane and then 166 ml of condensed chlorine were added thereto at 20° C. over 5½ hours. The mixture was stirred at 20°–25° C. over night and the mixture was then slowly added at 17° C. to a mixture of water-ice-hydrochloric acid. The mixture was then extracted with methylene chloride and the extracts were washed successively with hydrochloric acid, water and sodium bicarbonate solution. The extracts were dried and evaporated to dryness and the residue was chromatographed over silica gel. Elution with benzene yielded 217 g of a mixture of 1- and 3-chloro-benzosuberone.

STEP B: 1- and 3-chloro-6-bromo-benzosuberone mixture

A mixture of 656 g of cuprous bromide and 3200 ml of ethyl acetate was refluxed for 45 minutes and then a solution of 328 g of the product of Step A in 1600 ml of chloroform was added at reflux over 1 hour. The mixture was refluxed for another 3 hours while adding another 151 g of cuprous bromide. The mixture was cooled and filtered and the filtrate was washed with a sodium chloride solution, was dried and evaporated to dryness to obtain 465 g of a raw mixture of 1- and 3-chloro-6-bromo-benzosuberone which was used as is for the next step.

STEP C: 1- and 3-chloro-8,9-dihydro[5H]benzocyclohepten-5-one mixture 459 g of lithium carbonate and 459 g of lithium bromide were added to a solution of 465 g of the product of Step B in 5 liters of dimethylformamide and the mixture was heated to 110° C. for 2½ hours and was then cooled. The mixture was filtered and the filtrate was diluted with methylene chloride. The solution was washed with an aqueous sodium chloride solution, was dried and evaporated to dryness to obtain 397 g of a mixture of 1- and 3-chloro-8,9-dihydro[5H]benzocyclohepten-5-one.

The said product was then used as in the process of Example 1 to react with benzylamine to form a mixture of 1- and 3-chloro-7-benzylamino-6,7,8,9-tetrahydro[5H]benzocycloheptene-5-one. The latter product was then reduced with lithium aluminum hydride to a mixture of 1- and 3-chloro-5ξ-hydroxy-7-benzylamino-6,7,8,9-tetrahydro[5H]benzocycloheptene which was subjected to hydrogenolysis to form a mixture of 1- and 3-chloro-5ξ-hydroxy-7-amino-6,7,8,9-tetrahydro/5H/benzocycloheptene which was dehydrated to form a mixture of 1- and 3-chloro-7-amino-6,7-dihydro/5H/benzocycloheptene.

EXAMPLE 3

Tablets weighing 200 mg were prepared from 25 mg of 7-amino-6,7-dihydro[5H]benzocycloheptene hydrochloride and sufficient excipient of talc, starch, lactose and magnesium stearate.

PHARMACOLOGICAL DATA

A. Potentialization of effects of monoamine oxidase inhibitor

The administration of a monoamine oxidase inhibitor to mice induces a hyperactive movement of the animals which is able to be potentialized by an antidepressant. Using the procedure of Carlsson et al. [Brain Research, Vol. 12 (1969), p. 456], a dose of 100 mg/kg of nialamide was intraperitoneally administered to mice 30 minutes before the intraperitoneal administration of the tested product and the values of actimetric measurements were recorded every 30 minutes for 6 hours. Potentiation of the effects of nialamide for the tested product was expressed in increasing number of + signs for a determined dose in mg/kg. Under the test conditions, the compound of Example 1 had an activity corresponding to + + at 5 mg/kg and + + + at 20 mg/kg.

B. Potentiation of effects of L-dopa

The administration of L-dopa to mice pretreated 18 hours previously with iproniazide produced certain number of symptoms; muscular hypertonicity, hyperactivity, agitation, crying, aggressiveness, salivation and exophthalmy. The intensity of these effects is potentiated by administration of an antidepressant one hour before the administration of L-dopa. Male mices received intraperitoneally 75 mg/kg of iproniazide 18 hours before the start of the test and the tested product was intraperitoneally administered in aqueous solution in increasing doses. One hour later, L-dopa was intraperitoneally administered at a dose of 100 mg/kg and the different symptoms were observed 15 and 30 minutes later. They were evaluated on a scale of 0 to 3 for each animal and the totals for each dose were determined. The $ED_{50}$ dose which potentiates by 50% the L-dopa effects was determined to be about 20 mg/kg for the product of Example 1.

C. Acute toxicity

The $DL_{50}$ dose which kills 50% of mice after intraperitoneal administration of the tested compound was determined 48 hours later and the $DL_{50}$ for the compound of Example 1 was about 75 mg/kg.

BIOCHEMICAL STUDY

A. Inhibition of Serotonine uptake in vitro

The inhibition of serotonine (5HT) uptake was measured in impure synaptosomes prepared from the entire brain of a female rat 19 to 21 days old using the technique of Kannengiesser et al. [Biochemical Pharmacology, Vol. 22, (1973) p. 73]. Diverse concentrations of the products were placed in an incubator with the preparation at 37° C. for 5 minutes in the presence of 14 C-5HT at a concentration of $10^{-7}$ M. The 50% inhibiting concentration ($IC_{50}$), dose which inhibits by 50% the uptake of 14C-5HT in the synaptosomes was determined graphically and the $IC_{50}$ dose for the compound of Example 1 was about $2.4 \times 10^{-6}$ M.

B. Inhibition of Serotonine uptake in vivo

The tested products were intraperitoneally administered to groups of female rats 19 to 21 days old at doses of 5 to 20 mg/kg. After 30 minutes, the brain was removed and synaptosomes were prepared and placed in an incubator in the presence of 14 C-5HT as indicated in the previous test. The relative power of the products to inhibit the uptake of 14C-5HT was estimated with respect to a test effected with animals which did not receive the tested product and the activity was expressed in increasing number of + signs. The compound of Example 1 showed a + sign at a dose of 20 mg/kg.

Various modifications of the products and methods of the invention may be made without departing from the spirit or scope thereof and it should be understood that the invention is intended to be limited only as defined in the appended claims.

We claim:

1. A compound selected from the group consisting of 7-amino-6,7-dihydro[5H]benzocycloheptenes of the formula

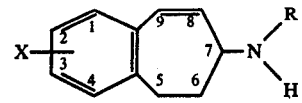

wherein X is selected from the group consisting of hydrogen, chlorine, bromine and iodine in 2- or 4-position of the ring when halogen and R is hydrogen and their non-toxic, pharmaceutically acceptable acid addition salts.

2. A compound of claim 1 selected from the group consisting of 7-amino-6,7-dihydro[5H]benzocycloheptene and its non-toxic, pharmaceutically acceptable acid addition salts.

3. An antidepressive composition comprising an effective amount of at least one compound of claim 1 and an inert pharmaceutical carrier.

4. A method of treating depressed states and psychoses in warm-blooded animals comprising administering to warm-blooded animals an antidepressantly effective amount of a least one active compound of claim 1.

5. The method of claim 4 wherein the active compound is selected from the group consisting of 7-amino-6,7-dihydro[5H]benzocycloheptene and its non-toxic, pharmaceutically acceptable acid addition salts.